United States Patent [19]

Huitson

[11] 4,220,661
[45] * Sep. 2, 1980

[54] PRESERVATIVE COMPOSITION

[75] Inventor: John J. Huitson, Banstead, England

[73] Assignee: BP Chemicals Limited, London, England

[*] Notice: The portion of the term of this patent subsequent to Jun. 20, 1995, has been disclaimed.

[21] Appl. No.: 905,735

[22] Filed: May 15, 1978

Related U.S. Application Data

[63] Continuation-in-part of Ser. No. 735,200, Oct. 26, 1976, abandoned.

[30] Foreign Application Priority Data

Nov. 27, 1975 [GB] United Kingdom ............... 38357/76

[51] Int. Cl.² .............................................. A01N 9/24
[52] U.S. Cl. ................................... 424/317; 424/164; 424/334; 424/343
[58] Field of Search ............... 424/166, 317, 140, 131, 424/154, 164, 334, 343

[56] References Cited

U.S. PATENT DOCUMENTS

| | | | |
|---|---|---|---|
| 3,786,086 | 1/1974 | Skov et al. | 260/541 |
| 3,899,588 | 8/1975 | Skov et al. | 424/317 |

OTHER PUBLICATIONS

Chemical Abstracts, vol. 56 (1961), p. 740h.
Chemical Abstracts, vol. 63 (1965), p. 6246c.
Chemical Abstracts, vol. 61 (1964), p. 14473g.
Becker et al., "J.A.C.S.", vol. 85 (1963), p. 157–159.

*Primary Examiner*—V. D. Turner
*Attorney, Agent, or Firm*—Brooks, Haidt, Haffner & Delahunty

[57] ABSTRACT

A liquid preservative composition comprising in aqueous solution a complex salt of an ion selected from $NH_4^+$ and a Group I or Group II metal ion and formic acid, the ratio of acid to cation being 4:1 on a chemical equivalent basis.

6 Claims, No Drawings

PRESERVATIVE COMPOSITION

The present invention relates to novel compositions suitable for industrial, agricultural and pharmaceutical applications and is a continuation in part of our copending U.S. application Ser. No. 735,200, filed on Oct. 26, 1976, now abandoned.

Hitherto saturated and unsaturated aliphatic carboxylic acids have only been sparingly used in industry and agriculture. The obnoxious odour of the free acids has made the handling of these acids unpleasant for the operatives and their corrosive nature has severely limited their use. It has been suggested in the past that this disadvantage may be overcome by employing the acids as their neutral salts or their esters. The obvious expedient of using the esters or neutral salts has been unsatisfactory since the acids on esterification or neutralisation lose a considerable amount of their activity.

It has now been found that by adding a base to an acid in aqueous solution in an amount which is less than the chemical equivalent required for full neutralisation, such compositions minimise to a substantial extent the odour and corrosivity of the acids without significant loss of activity of the free acid. In addition, it has surprisingly and unexpectedly been found that the base and acid combine under these conditions to form complexes. Such complexes have the added advantage that they exhibit considerably lower vapour loss relative to the free acids and hence retain the preservative activity on the substrate treated therewith for a longer period of time.

Accordingly, the present invention is a liquid composition comprising in aqueous solutions a complex salt of ammonium ions and/or ions of a metal selected from Group I and Group II of the Periodic Table due to Mendeleef, and formic acid, the ratio of acid to ammonium and/or metal ions being 4:1 on a chemical equivalent basis.

The compositions of the present invention may contain, in addition, one or more carboxylic acids selected from saturated and unsaturated aliphatic monocarboxylic acids having from 2-8 carbon atoms, preferably containing 2 to 4 carbon atoms. Acetic, propionic, n-butyric, isobutyric, n-valeric, 2-methylbutyric, levulinic, acrylic, sorbic and methacrylic acids are the most preferred.

The Group I and Group II metals of the Periodic Table due to Mendeleef are preferably selected from sodium, potassium, calcium and magnesium. Although metal ions such as copper, strontium and beryllium may also be used, it will be clear that such compositions can only be used for certain special applications eg involving pesticidal or fungicidal activity, due to the known toxic nature of the cation.

The minimum amount of water in the compositions of the present invention will depend upon the solubility of the complex salts contained therein. Thus the complex calcium and magnesium salts would be somewhat less soluble than the complex sodium and ammonium salts. The concentration of water would therefore be suitably between the minimum necessary to form a homogeneous solution up to a maximum of 90% by weight, preferably between 15 and 75% by weight of the total composition.

The compositions of the present invention may contain one or more of the complex salts. For example, the composition may contain ammonium tetraformate, sodium tetraformate, calcium octaformate, magnesium octaformate and mixtures thereof.

The complex salt may be prepared by mixing formic acid with a calculated amount of a base of the desired cation in an aqueous medium. For example, in preparing compositions containing the ammonium ion the acid may be mixed with a concentrated aqueous ammonia solution. On the other hand, for preparing compositions containing the calcium ion, a full calcium salt of the acid may be dissolved in an appropriate amount of the free acid or the free acid may be partially neutralised by lime or reacted with limestone.

The compositions of the present invention with a suitable cation may be used as a preservative for animal feedstuffs and agricultural crops to prevent growth of mould, bacteria and fungi. This may be achieved by applying the composition to the desired substrate as hereinafter defined.

By the term "substrate" is meant here and throughout the specification grass, agricultural crops and/or compounded animal feedstuffs and materials used in preparation thereof such as barley, wheat, oats, rye, maize, rice, hay, straw, silage, dried grass, tick beans, soya beans, bagasse, sunflower seed, sugar cane, rape seed, groundnuts, fish meal, meat and bone meal, buckwheat chaff and wood shavings. The compositions of the present invention are particularly suitable as silage additives, for the control of bacteria such as salmonellae and in the production of liquefied protein from fish, animal offal and the like.

The compositions of the present invention when used as a preservative may also contain other conventional additives, in particular those with fungicidal or bactericidal properties, such as formalin, methanol, dehydroacetic acid and bisulphites.

Compositions containing tetraformates, especially ammonium tetraformate, formaldehyde and methanol are preferred. These are found to be superior to the corresponding diformate compositions with the same additives especially in relation to the relatively lower amount of free ammonia liberated and the relatively greater amount of lactic acid formed during the ensiling process.

The amount of composition used for the preservation of a substrate would depend not only on the substrate to be preserved but also on the acidic and cationic ingredients thereof. For example, copper which is nutritionally valuable and is a known growth promoter in animal feed would be used in low concentrations. On the other hand, compositions containing ammonium ions can be used within a wide range of concentrations without any deleterious effect. Thus, the liquid compositions of the present invention when applied as a preservative to a substrate would suitably be at a rate of between 0.1 and 5% of the inorganic complex salts based on the weight of the substrate treated, preferably between 0.1 and 2.5% by weight of the substrate treated. The liquid compositions may be applied to the substrates before, during or after harvest or processing.

Other applications of the compositions of the present invention include use in industry for removal of scales from pipes and boilers. In the pharmaceutical industry one of the uses may be in the treatment of fungal infections such as athlete's foot. Such solutions also exhibit buffering activity and may find use in photographic applications and as assistants in the dyeing of textiles. The ammonium and sodium ion containing solutions may be useful as antifreezes. Copper containing solutions may be used for example as wood preservatives and in crop fungicides.

The principal advantages of using the compositions of the present invention are that:

(a) they are less caustic to skin and hence considerably safer to the operative, 46 g, 1 mole, formic acid) with concentrated aqueous ammonia solution (12.9 g solution containing 33% w/w $NH_3 = 0.25$ mole, 4.25 g).

(C) A solution containing 72.5% w/w of the salt was also prepared by appropriate dilution of the product obtained from preparation (B).

TABLE

PHYSICAL PROPERTIES OF AMMONIUM TETRAFORMATE AND FORMIC ACID SOLUTIONS

|  | 85% w/w AMMONIUM TETRAFORMATE SOLUTION (ATF) | 85% w/w FORMIC ACID | 75.2% w/w AMMONIUM TETRAFORMATE SOLUTION (ATF) | 72.5% w/w FORMIC ACID |
|---|---|---|---|---|
| pH | 2.8 | off scale | 2.9 | off scale |
| Density at 20° C. (kg/liter) | 1.222 | 1.195 | 1.181 | 1.171 |
| Viscosity c/s at 20° C. | 4.36 | 1.63 | 2.39 | 1.52 |
| Crystallisation temp °C. | ca $-20°$ C. | $-20$ | $-36$ | $-45$ |
| Flash point, Pensky-Martens (closed cup) °C. | 70 | 68 | 70 | Not Determined |
| Concentration in Vapour |  |  |  |  |
| Ammonia  mg/m$^3$ | None Detected | — | None Detected |  |
| Formic Acid  mg/m$^3$ | 764 | 1,547 | 649 | 1,356 |
| Carbon Monoxide  mg/m$^3$ | 1,290 | 4,590 | 880* | Not Determined |
| % Loss on Evaporation (140 hours) | 5.7 | 28.0 | 9.7 | 22.8 |

*value for 75% w/w ATF solution (b) they are less corrosive to metals than the free acids, (c) they do not remove paint and grease and so do not promote deterioration of equipment, (d) they have a lower vapour pressure than the free acids and hence not only reduce environmental hazards due to evaporation but also make more efficient use of the preservative composition applied on the substrate, (e) they do not attack soft seals and pipes and hence facilitate equipment design, (f) they reduce, and in some cases eliminate, the obnoxious odour of the preservative acids, (g) they are appreciably more active than the neutral salts and only marginally less active than the free acids, (h) they have a greater solubility in water than the neutral salts and hence facilitate formulation, (i) they can be used as a medium for introducing nutritionally beneficial cations into the substrates preserved, (j) they have higher flash points than the free acids and hence present less of a fire hazard, (k) they are more stable towards decomposition to carbon monoxide than free formic acid.

The invention is further illustrated with reference to the following Examples.

EXAMPLES

1. PREPARATION (A) A 85% w/w solution of ammonium tetraformate was prepared by the reaction of 98–100% strength formic acid (1 mole, 46 g) with concentrated aqueous ammonia solution (12.9 g solution containing 33% w/w $NH_3 = 0.25$ mole, 4.25 g).

(B) A 75% w/w solution of the salt was prepared by dilution of the product from preparation (A), or by reaction of 85% strength formic acid (54.1 g containing (a) No ammonia was detected in the saturated vapours above the 72.5% and 85% w/w ATF solutions. Hence during normal use of the salts, no problem is envisaged in exceeding the Threshold Limit Value for Ammonia (18 mg/m$^3$). The concentration of formic acid in the vapours above the ATF solutions was found to be about half that in the vapours above corresponding strength solutions of formic acid. Thus any reduction in losses will help to overcome operator discomfort during use. Again this correlates with the Odour Panel results (Table 5) and evaporation tests.

(b) Formic acid is known to decompose to carbon monoxide and water. The concentration of carbon monoxide in the saturated vapour above the test solution was therefore taken as a measurement of the rate of decomposition of the acid in the solution. The results show that there is significantly less carbon monoxide in the vapours above the 72.5% and 85% ATF solutions than in the vapours above corresponding aqueous formic acid solutions. Hence the indications are that ATF is less susceptible to decomposition to carbon monoxide.

(c) The relatively high pH's of the ATF solutions compared to corresponding formic acid solutions indicates that such solutions should be less corrosive to farm machinery and safer for operators to handle.

| TEST SOLUTION | CORROSION RATE mm YEAR | pH OF TEST SOLUTION |
|---|---|---|
| 0.6% m/m Formic Acid in Water | 0.6 | 2.7 |
| 0.6% m/m Ammonium Tetraformate (ATF) | 0.4 | 3.2 |

TABLE 3

CORROSIVITY OF FORMIC ACID AND AMMONIUM TETRAFORMATE SOLUTION TOWARDS CLOTHING

| TYPE OF MATERIAL | EFFECT ON MATERIAL | | EFFECT ON DYE | |
|---|---|---|---|---|
|  | 85% w/w ATF SOLUTION | 85% FORMIC ACID | 85% w/w ATF SOLUTION | 85% FORMIC ACID |
| Brushed Cotton | None Detected | None Detected | Held Fast | The purple colour changed |

TABLE 3-continued
CORROSIVITY OF FORMIC ACID AND AMMONIUM TETRAFORMATE SOLUTION TOWARDS CLOTHING

| | EFFECT ON MATERIAL | | EFFECT ON DYE | |
|---|---|---|---|---|
| TYPE OF MATERIAL | 85% w/w ATF SOLUTION | 85% FORMIC ACID | 85% w/w ATF SOLUTION | 85% FORMIC ACID |
| shades of purple and blue | | | | to blue when wet. It returned to its original purple colour on drying but with some evidence of slight fading. |
| Crimplene purple and white | None Detected | None Detected | Held Fast | Held Fast |
| Polyester Jersey brown and yellow | None Detected | None Detected | Held Fast | Held Fast |
| Brushed Nylon red | None Detected | The area covered by the solution dissolved rapidly. | Held Fast | — |
| Nylon Lining | None Detected | The area covered by the solution dissolved rapidly. | Held Fast | — |

The material under test was stretched tightly over a glass beaker and held in position by a rubber band. 2 ml samples of 85% w/w formic acid and 85% w/w ATF solution were dropped by pipette onto the material.
The 85% w/w ATF solution had no noticeable effect upon cotton, crimplene, polyester or nylon fabrics. In contrast, aqueous formic acid rapidly dissolved nylon. These results underline the safer handling characteristics of ATF.

TABLE 4
PAINT STRIPPING PROPERTIES OF AMMONIUM TETRAFORMATE AND FORMIC ACID SOLUTIONS

Mild steel test-pieces with a cellulose primer and a red top coat were immersed in the test solutions for 6 hours. The results are reported below.

| TIME IMMERSED | 85% AND 72.5% w/w FORMIC ACID SOLUTIONS | 85% AND 72.5% AMMONIUM TETRAFORMATE (ATF) |
|---|---|---|
| 20 minutes | Top coat dissolving and base metal visible at the edges of the test-pieces. | No noticeable effect |
| 1 hour | Paint very soft | Slight indications that paint was thinning at the edges of the test-pieces. |
| 6 hours | Considerable amount of top coat removed. Paint very soft and tacky. Test-pieces removed and carefully washed with water. | Test-pieces removed and washed with water. Paint soft but not tacky. |
| Dried overnight | Paint still very tacky | Paint firm and showing little evidence of immersion. |

TABLE 5
ODOUR PANEL RESULTS

The odour of the test solutions was assessed by a panel. Observations are given below.

| Solution | Unpleasant Odour | Acceptable Odour |
|---|---|---|
| 85% w/w Formic Acid Solution | 100% | |
| 75% w/w Ammonium Tetraformate Solution (ATF) | 15% | 85% |

2. AMMONIUM TETRAFORMATE AS A SILAGE ADDITIVE

In each experiment 1 Kg samples of a freshly harvested 50/50 mixture (86.5% moisture content) of Cocksfoot grass/Europa Lucerne were treated with the composition under test, and stored under anaerobic conditions for 3 months. After this time the silages were analysed for water soluble carbohydrates, free ammonia, n-butyric acid and lactic acid. The odours of the silages were also noted. A criterion of a good silage is an acceptable odour, high lactic acid and water soluble carbohydrates concentrations and low concentrations of free ammonia and n-butyric acid. In these experiments a 75% aqueous solution of ammonium tetraformate was evaluated, together with a mixture of ammonium tetraformate (45% w/w), formaldehyde (14.8% w/w), methanol (4.8% w/w), and water (35.4% w/w). The latter mixture did not precipitate any formaldehyde polymer on standing. Silage analyses are presented below. Results obtained either without additive, or with 85% aqueous formic acid are included for comparison.

The results indicated that addition of ammonium tetraformate, especially mixed with formalin, improved the quality of silage.

| ADDITIVE | TREATMENT LEVEL | | CHEMICAL ANALYSIS OF SILAGE (% w/w - WET WEIGHT BASIS) | | | | | |
|---|---|---|---|---|---|---|---|---|
| | % v/w | % w/w ACTIVE INGRED(S) | WATER SOLUBLE CARBO-HYDRATE | FREE NH$_3$ | n-BUTYRIC ACID | LACTIC ACID | pH OF SILAGE JUICE | ODOUR OF SILAGE |
| None | — | — | 0.01 | 0.30 | 0.85 | NIL | 6.1 | Unpleasant |
| 85% w/w Formic Acid in Water | 0.22 | 0.22 | 0.07 | 0.08 | NIL | 2.21 | 4.4 | Sweet |
| 85% Formic Acid in Water | 0.45 | 0.46 | 0.10 | 0.07 | NIL | 3.53 | 4.0 | Sweet |
| 75% w/w Ammonium Tetraformate in Water | 0.22 | 0.20 | 0.06 | 0.11 | NIL | 1.17 | 5.0 | Sweet |
| 75% w/w Ammonium Tetraformate in Water | 0.45 | 0.40 | 0.09 | 0.10 | NIL | 2.78 | 4.3 | Sweet |
| 45% w/w Ammonium Tetraformate, 14.8% Formaldehyde, 4.8% Methanol, 35.4% H$_2$O | 0.22 | 0.16 | 0.05 | 0.10 | NIL | 1.82 | 4.9 | Sweet |
| Methanol, 35.4% H$_2$O | 0.45 | 0.33 | 0.09 | 0.09 | NIL | 3.15 | 4.4 | Sweet |

3. AMMONIUM TETRAFORMATE AS A SALMONELLA CONTROL AGENT

Animal meat and bone meal obtained commercially was analysed as indicated below for the Most Probable Number (MPN) of Salmonellae. If the MPN was considered to be too low then small amount of meal were incubated after remoistening to about 25% by mass. The incubated meal was then diluted with Salmonellae-free meal to give the approximate MPN required. Portions (100 g) of the contaminated meal were sprayed with the formulation under test using a chromatography spray. The samples were left for three days at ambient temperature before a MPN determination was carried out. A control sample, which had not been treated according to the invention, was used in each experiment to give the initial MPN of Salmonellae present in the meal. The following analytical method was used.

(i) From each sample the following sub-samples were taken:
3×10 g
3×1 g
3×0.1 g (ii) Each sub-sample was pre-enriched in buffered peptone water in such a quantity that a 1 in 10 dilution was produced. These suspensions were incubated at 37° C. for 18 hours.

(iii) A sample was taken from each pre-enriched suspension, and added to tetrathionate broth containing 0.001% w/w brilliant green agar. The following dilutions were used:

10 cm$^3$ of the 10 g sample pre-enrichment suspensions +90 cm$^3$ tetrathionate broth.

1 cm$^3$ of the 1 g sample pre-enrichment suspensions + 9 cm$^3$ tetrathionate broth.

0.5 cm$^3$ of the 0.1 g sample pre-enrichment suspensions +4.5 cm$^3$ tetrathionate broth.

These enrichment broths were incubated at 42° C. for 28 hours.

(iv) A loopful of the enrichment broths was transferred to 10 cm$^3$ of "M" broth and incubated at 37° C. for 18 hours. The presence of salmonellae was determined by the agglutination reaction with pooled antisera. By reference to statistical tables complied by De Man, J. C. in "The Probability of the Most Probable Number" European Journal of Appl. Microbiol, 1,67–68 (1975), the most probable number (MPN) of salmonellae in the original sample was determined from the number of salmonella positives/negatives obtained for each sub-sample.

Treated and untreated samples were left at ambient temperature for three days before MPN determinations. The moisture content of the meal was initially 8% by mass.

TABLE 7

| Formulation | % Formic Acid | % Water |
|---|---|---|
| A | 85.0 | 15.0 |
| B | 75% Ammonium tetraformate solution | |

| Exp No | Sample control | Formu-lation | % Product Applied | % Formic Acid | pH | MPN/ 100g |
|---|---|---|---|---|---|---|
| 1 | Control* | None | | | 6.05 | 40 |
| | (a) | A | 1.9 | 1.6 | 4.9 | <1 |
| 2 | Control* | None | | | 5.8 | 40 |
| | (b) | B | 4.0 | 2.1 | 4.65 | <1 |
| 3 | Control* | None | | | 6.0 | 200 |
| | (c) | B | 2.0 | 1.0 | 5.3 | 40 |

*Samples obtained from different sources.

The results show that ammonium tetraformate is as effective as formic acid against Salmonella. Admittedly, the tetraformate is employed in marginally higher concentrations, but this has to be offset against the relatively lower corrosivity, absence of obnoxious odour and absence of evaporative losses especially when treating hot meals.

4. USE OF AMMONIUM TETRAFORMATE IN THE PRODUCTION OF FISH SILAGE

Liquid fish protein, suitable for use as an animal feed, can be made from whole or parts of fish that have been minced and acidified with 3.5% w/w formic acid. It has now been found that a similar liquid product can be produced by the addition of the less corrosive, safer to handle, ammonium tetraformate solution (75% w/w). The results presented below refer to the liquefaction of minced blue whiting:

TABLE 8

| % w/w addition of ammonium tetraformate solution (75% w/w) | pH Product |
|---|---|
| 3.0 | 4.3 |
| 4.0 | 4.2 |
| 5.0 | 4.0 |

5. COMPARISON OF AMMONIUM TETRAFORMATE WITH AQUEOUS FORMIC ACID AND AMMONIUM DIFORMATE

1 Kg samples of a freshly harvested 50/50 mixture of Cocksfoot and Europa Lucerne silage which had the following analysis at the time of treatment:
Moisture content: 86.5% w/w
Dry matter: 13.5% w/w
pH: 6.27
Total nitrogen: 4.35% w/w (dry basis)
Buffering capacity: 5.8 m equiv/100 g of sample were ensiled in gas jars on Oct. 28, 1976. Duplicate samples were treated at 0.22 and at 0.45% v/m with the following materials (except (f) below which was applied at the 0.22% v/w level only):
a. Formic acid (85% w/w aqueous solution).
b. Ammonium Diformate (75% w/w aqueous solution) —$HCO_2NH_4 \cdot HCO_2H$.
c. Ammonium Tetraformate (75% w/w aqueous solution)—$HCO_2NH_4 \cdot 3HCO_2H$.
d. A mixture comprising
  45% w/w Ammonium Diformate
  16% w/w Formaldehyde
  5% w/w Methanol
  34% w/w Water
e. A mixture comprising
  45% w/w Ammonium Tetraformate
  16% w/w Formaldehyde
  5% w/w Methanol
  34% w/w Water
f. A mixture comprising
  50% w/w Formic Acid
  (50% w/w Propionic Acid
Five untreated Control samples were ensiled.

The samples were kept in the gas jars fitted with fermentation locks until Jan. 25/26, 1977 (3 months' ensiled) when the jars were opened and the contents analysed to determine the effect of the various additives on primary fermentation.

As each jar was opened the smell of the silage was noted. All the Control samples had obnoxious odours. Slightly unpleasant odours were obtained from silages which had been treated with 0.22% v/m of Ammonium diformate.

Silages which had been treated with the rest of the additives had a sweetish odour.

All the silages were of a reasonable appearance and were mould free.

After ensilage the concentrations of water soluble carbohydrates, free ammonia, carboxylic acids and pH's of the treated and untreated silages were analysed. The results are tabulated below (see Table 9).

TABLE 9 pH and Composition of Silages

| Additive | Treatment Level % v/m | pH of Juice | Free Ammonia | WSC** as Glucose | Lactic Acid | Acetic Acid | Propionic Acid | i-Butyric Acid | n-Butyric Acid | i-Valeric Acid | n-Valeric Acid |
|---|---|---|---|---|---|---|---|---|---|---|---|
| 1 85% w/w formic acid aqueous solution | 0.22 | 4.4 | 0.08 | 0.073 | 2.21 | 1.20 | 0.09 | | | | |
| 2 | 0.45 | 3.95 | 0.065 | 0.098 | 3.53 | 1.03 | 0.02 | | | | |
| 3 75% w/w ammonium diformate solution | 0.22 | 5.4 | 0.155 | 0.027 | 1.10 | 1.88 | 0.08 | | | | |
| 4 | 0.45 | 4.7 | 0.135 | 0.056 | 2.09 | 1.53 | 0.09 | | | | |
| 5 75% w/w ammonium tetraformate solution | 0.22 | 5.0 | 0.11 | 0.056 | 1.17 | 1.73 | 0.15 | | | | |
| 6 | 0.45 | 4.3 | 0.095 | 0.092 | 2.78 | 1.28 | 0.06 | | | | |
| 7 45% w/w ammonium diformate 16% w/w formaldehyde 5% w/w methanol 34% w/w water | 0.22 | 5.15 | 0.135 | 0.056 | 1.16 | 1.47 | 0.08 | | | | |
| 8 | 0.45 | 4.45 | 0.105 | 0.111 | 2.06 | 1.13 | 0.11 | | | | |
| 9 45% w/w ammonium tetraformate 16% w/w formaldehyde 5% w/w methanol 34% w/w water | 0.22 | 4.85 | 0.10 | 0.048 | 1.82 | 1.49 | 0.08 | | | | |
| 10 | 0.45 | 4.4 | 0.09 | 0.089 | 3.15 | 1.23 | 0.05 | | | | |
| 11 50% w/w formic acid: 50% w/w propionic acid | 0.22 | 4.8 | 0.11 | 0.056 | 1.59 | 1.89 | 0.20 | | | | |
| 12 Control | Nil | 6.1 | 0.30 | 0.014 | ND* | 1.32 | 0.22 | 0.10 | 0.85 | 0.18 | 0.11 |

*ND - Not Detected
**WSC - Water Soluble Carbohydrate

The results above indicate that the five formulations tested can be placed in the following approximate order of decreasing activity as silage additives based on lactic acid content:

85% aqueous formic acid > Ammonium Tetraformate/Formalin > Ammonium Tetraformate > Ammonium Diformate/Formalin > Ammonium Diformate The formic/propionic acid mixture has been excluded from this list because data are only available for one treatment level (0.22% v/w). Indications are that its activity lies between Ammonium Tetraformate/Formalin and Ammonium Tetraformate.

The results also indicate that the activities of both ammonium di- and tetraformate/formalin mixtures were greater than the solutions of the salts on their own. It is worth noting here that ammonium acid formates/formalin/methanol mixtures are stable towards precipitation of formaldehyde polymers.

I claim:

1. A liquid preservative composition comprising: (a) an aqueous solution of a salt of formic acid and a cation selected from the group consisting of ammonium, sodium, potassium, calcium and magnesium ions, the ratio of acid to cations in said salt being 4:1 on a chemical equivalent basis and the concentration of water in said solution being in the range of about 15 to 90% by weight based on the total weight of the composition, and (b) at least one monocarboxylic acid selected from the group consisting of acetic acid, propionic acid, isobutyric acid, n-butyric acid, n-valeric acid, 2-methyl butyric acid, levulinic acid, acrylic acid, sorbic acid, and methacrylic acid.

2. A liquid preservative composition comprising: (a) an aqueous solution of a salt of formic acid and a cation selected from the group consisting of ammonium, sodium, potassium, calcium and magnesium ions, the ratio of acid to cations in said salt being 4:1 on a chemical equivalent basis and the concentration of water in said solution being in the range of about 15 to 90% by weight based on the total weight of the composition, and (b) at least one bactericidal or fungicidal additive selected from the group consisting of formalin, methanol, dehydroacetic acid and bisulphite.

3. A process for treating grass, agricultural crops, animal feedstuffs, silage, or fish protein which comprises applying to one of said materials an effective preservative amount of an aqueous solution of a salt of formic acid and a cation selected from the group consisting of ammonium, sodium, potassium, calcium, and magnesium ions, the ratio of acid to cations in said salt being 4:1 on a chemical equivalent basis and the concentration of water in said solution being in the range of about 15 to 90% by weight based on the total weight of the composition.

4. A process according to claim 3 wherein the liquid composition is used as a silage additive.

5. A process according to claim 3 wherein the liquid composition is used for controlling salmonella.

6. A process according to claim 3 wherein the liquid composition is applied to fish protein.

* * * * *

UNITED STATES PATENT AND TRADEMARK OFFICE
CERTIFICATE OF CORRECTION

PATENT NO. : 4,220,661

DATED : September 2, 1980

INVENTOR(S) : JOHN J. HUITSON

It is certified that error appears in the above-identified patent and that said Letters Patent are hereby corrected as shown below:

Col. 4, line 7, after "TABLE" insert --1--.

Col. 4, line 52, insert the following:

-- TABLE 2

CORROSIVITY OF DILUTE SOLUTIONS TOWARDS MILD STEEL

An attempt was made to determine the weight loss from polished mild steel test-pieces (BS 4360, grade 43A), after immersing in dilute solutions of ammonium tetraformate and formic acid (0.6% w/w solutions), for period of 171 hours. The mild steel weight losses was determined and the results are tabulated below.--

Col. 4, line 58, after the table insert the following:

--The corrosion tests involving immersing mild steel test-pieces in the concentrated solutions of formic acid and ATF were inconclusive, owing to the deposition of crystals on the metal surfaces. However, corrosion tests conducted with the above dilute solutions (to simulate corrosivity when the concentrated solutions are used as silage additives and are diluted by the water present in the silage), indicate that the ATF is less corrosive than formic acid. The results correlate with the pH's of the dilute solutions.--

UNITED STATES PATENT AND TRADEMARK OFFICE
CERTIFICATE OF CORRECTION

PATENT NO. : 4,220,661

DATED : September 2, 1980

INVENTOR(S) : JOHN J. HUITSON

It is certified that error appears in the above-identified patent and that said Letters Patent are hereby corrected as shown below:

Col. 5, line 51, after "TABLE 4", insert the following:

--A considerable amount of the paint film was removed from painted test-pieces after immersing in 72.5% w/w and 85% w/w formic acid for 6 hours. In contrast the paint film was intact after immersing in 72.5% and 85% w/w ATF solutions for the same period.--

Col. 5, line 61, after "TABLE 5", insert the following:

--The majority of an Odour Panel (85%) found the odour of a 75% w/w ATF solution acceptable. In contrast 100% of the panel found the odour of 85% w/w aqueous formic acid unpleasant.--

Cols. 7 and 8, top line, insert --TABLE 6--.

Signed and Sealed this

Twenty-fourth Day of March 1981

[SEAL]

Attest:

RENE D. TEGTMEYER

Attesting Officer  Acting Commissioner of Patents and Trademarks

UNITED STATES PATENT AND TRADEMARK OFFICE
CERTIFICATE OF CORRECTION

PATENT NO. : 4,220,661
DATED : September 2, 1980
INVENTOR(S) : JOHN J. HUITSON

It is certified that error appears in the above-identified patent and that said Letters Patent are hereby corrected as shown below:

Title page, change the asterisk [*] Notice to read as follows:

-- [*] Notice: The portion of the term of this patent subsequent to December 18, 1996 has been disclaimed.--

Signed and Sealed this

Fourth Day of August 1981

[SEAL]

Attest:

GERALD J. MOSSINGHOFF

Attesting Officer Commissioner of Patents and Trademarks